United States Patent
Nagatomi et al.

(10) Patent No.: US 8,188,017 B2
(45) Date of Patent: May 29, 2012

(54) ORGANIC MOLYBDENUM COMPOUNDS AND OIL COMPOSITIONS CONTAINING THE SAME

(75) Inventors: Eiji Nagatomi, Tokyo (JP); Noriaki Shinoda, Tokyo (JP); Yoshihiko Aihara, Tokyo (JP)

(73) Assignee: Shell Oil Company, Houston, TX (US)

( * ) Notice: Subject to any disclaimer, the term of this patent is extended or adjusted under 35 U.S.C. 154(b) by 156 days.

(21) Appl. No.: 12/525,355

(22) PCT Filed: Feb. 1, 2008

(86) PCT No.: PCT/EP2008/051256
§ 371 (c)(1),
(2), (4) Date: Feb. 22, 2010

(87) PCT Pub. No.: WO2008/092944
PCT Pub. Date: Aug. 7, 2008

(65) Prior Publication Data
US 2010/0144568 A1    Jun. 10, 2010

(30) Foreign Application Priority Data
Feb. 1, 2007 (JP) .................. 2007-023130

(51) Int. Cl.
*C10M 135/18* (2006.01)
(52) U.S. Cl. ............... 508/362; 508/268; 508/388
(58) Field of Classification Search .................. 508/363, 508/268, 362, 388
See application file for complete search history.

(56) References Cited

U.S. PATENT DOCUMENTS
5,126,465 A    6/1992 Greaney et al. .......... 556/61

FOREIGN PATENT DOCUMENTS

| | | |
|---|---|---|
| DE | 3717143 | 12/1988 |
| EP | 0668342 | 8/1995 |
| EP | 0776959 | 6/1997 |
| EP | 1029029 | 8/2000 |
| EP | 1741772 | 10/2007 |
| GB | 789383 | 1/1958 |
| JP | 48056202 | 8/1973 |
| JP | 52019629 | 2/1977 |
| JP | 52106824 | 9/1977 |

(Continued)

OTHER PUBLICATIONS

G.A. Domrachev et al., Formation of Molybdenum Disulfide Upon Decomposition of Organic Complexes Containing A MO-S Bond, Zhurnal Obshchey Khimii, 1989, V. 59, No. 6, p. 1351-1355.*

(Continued)

*Primary Examiner* — James Goloboy
*Assistant Examiner* — Taiwo Oladapo (57) ABSTRACT

The present invention provides novel organic molybdenum compounds, the use thereof as friction-modifiers and lubricating compositions which contain said compounds.

The organic molybdenum compounds can be represented by the general formula (1) which is indicated below, General Formula (1)

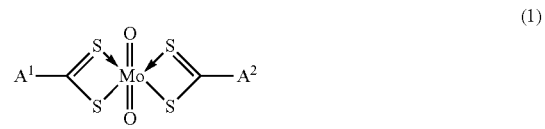

wherein $A^1$ and $A^2$ are heterocyclic rings which may have substituent groups.

6 Claims, 1 Drawing Sheet

FOREIGN PATENT DOCUMENTS

| | | |
|---|---|---|
| JP | 62161992 | 7/1987 |
| JP | 3495764 | 2/2004 |
| WO | WO9721788 | 6/1997 |
| WO | WO9941332 | 8/1999 |
| WO | WO0008115 | 2/2000 |
| WO | WO0014179 | 3/2000 |
| WO | WO0014183 | 3/2000 |
| WO | WO0014187 | 3/2000 |
| WO | WO0014188 | 3/2000 |
| WO | WO0015736 | 3/2000 |
| WO | WO0118156 | 3/2001 |
| WO | WO0157166 | 8/2001 |

OTHER PUBLICATIONS

XP-002476213, 1991.*

Domrachev, G.A., et al: "Molybdenum disulfide formation during decomposition of organic compounds containing a molybdenum-sulfur bond", XP002475834, 1989.

Cousins, M., et al: "Some oxo-and oxochlorocyclopentadienylmolybdenum complexes", XP002475835, 1964.

Green, Malcolm L.H., et al: Interconversion of oxo and imido ligands at a dimolybdenum center: molecular and electronic structure of [{Mo(.eta.-C5H4Me) (NPh) (.mu.-NPh)}], XP002475836, 1990.

Saurenz, Dirk, et al: "Cyclopentadienylmolybdenum(VI) and molybdenum(V) oxo chemistry: new synthetic and structural features", XP002475837, 2002.

Hogarth, Graeme, et al: "Electrochemistry of dimolybdenum complexes containing oxo, imido, and sulfide moieties. A measure of their relative .pi.-donor abilities?", XP002475838, 1991.

Bursten, Bruce E., et al: "Electronic structure of piano-stool dimmers. 8. Electronically induced conformational changes in high-valent bimetallic chalcogen complexes of the type [CpML]2(.mu.-L)2 (M=molybdenum rhenium; L=S, O)", XP002475839, 1989.

Gun, Jenny, et al: "Reduction of [(C5Me5)2Mo2O5] and [(C5Me5)2Mo2O4] in methanol/water/trifluoroacetate solutions investigated by combined on-line electrochemistry/electrospray-ionization mass spectrometry", XP002475840, 2003.

Brunner, Henri, et al: "Preparation and reactivity of binuclear oxo(pentamethylcyclopentadienyl)molybdenum sulfides", Journal of Organometallic Chemistry, 331(1), pp. 45-52, 1987, XP002475832, 1987.

Journal of Organometallic Chemistry 331(1), pp. 45-52, XP002475833, 1987.

Tanner, L.D., et al: "Structures and reactivities of cyclopentadienylmolybdenum complexes with oxo and sulfide ligands", XP002475841, 1988.

Reuter, U. et al: "On chalcogenolates. LXX. Experiments to prepare tetrathiooxalates. About alkylthio-1, 3-dithiole-2-thiones" XP002476509, 1976.

Maejima, Seiju et al: "Surface reinforcement of an inorganic porous material" XP002473509, 1986.

Unoura, Kei et al: "Substituent effects of cis-dioxobis(dithiocarbamato)molybdenum(VI) on redox properties: redox potentials for one-electron reduction and second=order rate constants for oxygen atom transfer" XP002476206, 1998.

Sovilj, S. P. et al; "Molecular modelling of new dioxomolybdenum (VI) complexes with heteroalicyclic dithiocarbamates. In Silico models for metal-implant coating within living systems" XP002476207, 2006.

Gnecco, J. A. et al: "Catalytic epoxidation of cyclohexene using molybdenum complexes" XP002476208, 2004.

Sovilj, S. P. et al: "Dioxomolybdenum (VI) complexes of methylpiperidinodithiocarboxylates" XP002476209, 2003.

Macial, Benigno et al: "An EXAFS study of Mo(VI) and Mo (V) complexes with proline dithiocarbamate" XP002476210, 1999.

Stergiou, Anagnostis C. et al: "Spectroscopic investigation of dichloro and hydrazido(2-) derivatives of bis9dithiocarbamato)dioxomolybdenum(VI) compounds. Crystal and molecular structure of bis(diisobutyldithiocarbanato) (N,N-dimethylhydrazido(2-)-N')oxomolybdenum(VI)" XP002476211, 1994.

Bhat, G. S. et al: "Synthesis and characterization of lead(II), bismuth (III), titanium(IV), selenium(IV), thorium(IV), dioxomolybdenum(VI) and dioxouranium(VI), hexamethylenimjnecarbodithioate and their biological activities" XP002476212, 1994.

Nair, B. Gopalakrishnan et al: "A novel series of cis-dioxomolybdenum(VI) carbodithioate complexes" XP002476213, 1991.

Moloy, Kenneth G.: "Oxygen atom transfer reactions, Epoxide deoxygenation by bis(diethyldithiocarbamato)oxomolybdenum" XP002476214, 1988.

Berzina, S. et al: "Two-phase stability constants of some 3-pyrorolecarbodithioates and 3-indoleacrbodithioates" XP002476215, 1976.

Byr'Ko, V. M. et al: "Composition and structure of mlybdenum (V, VI)5-phenyl-1-pyrazolinedithiocarbamates" XP002476216, 1973.

* cited by examiner

ORGANIC MOLYBDENUM COMPOUNDS AND OIL COMPOSITIONS CONTAINING THE SAME

The present application claims priority from PCT/EP08/051256, filed 1 Feb. 2008, which is incorporated by reference and which claims priority from JP 2007-023130, filed 1 Feb. 2007.

FIELD OF THE INVENTION

The invention relates to novel organic molybdenum compounds, the use thereof as friction-modifiers and lubricating compositions which contain said compounds.

BACKGROUND OF THE INVENTION

Friction-modifiers (friction-adjusting agents) are used for adjusting the friction characteristics of a lubricant to an appropriate level. Friction-modifiers which reduce friction are used in lubricating compositions such as gear oils and engine oils with a view to reducing fuel costs. Friction-modifiers which raise friction are used for maintaining a certain high friction level in the lubricating compositions which are used in the wet-type clutch part of an automatic gear box. Many types of such friction-modifiers have been proposed.

The organic molybdenum compounds are the most typical of these friction-modifiers and, as shown in "Shinban Sekiyu Seihin Tenkasai" (New Edition, Additives for Petroleum Products), by Toshio SAKURAI, Saiwai Shobo Co., published 25 Jul. 1986, these organic molybdenum compounds are compounds which have two molybdenum atoms in one molecule as shown in formulae (2) and (3) below.

Formula (2)

(Dithiophospate Type)

Formula (3)

(Dithiocarbamate Type)

(Those compounds for which in this formulae x=0 and y=4, those for which x+y=4, and those for which x≧2 are insoluble in oil and the others are oil-soluble.)

Furthermore, compounds in which the element molybdenum is included twice in one molecule have been disclosed in Japanese Patent No. 3495764, Japanese Examined Patent Publication 45-24562, Japanese Unexamined Patent Application Laid Open 52-19629, Japanese Unexamined Patent Application Laid Open 52-106824 and Japanese Unexamined Patent Application Laid Open 48-56202.

A problem with catalyst poisoning in the apparatus which is used for cleaning-up the exhaust gas arises when compounds which contain phosphorus in the molecule as shown in the aforementioned general formula (2) are added to engine oils and there is a demand for compounds which are phosphorus-free.

SUMMARY OF THE INVENTION

The purpose of the invention is to provide novel organic molybdenum compounds, the use thereof as friction-modifiers and lubricating compositions which contain said compounds.

DETAILED DESCRIPTION OF THE PREFERRED EMBODIMENTS

General Formula (1)

In this formula $A^1$ and $A^2$ are heterocyclic rings which may have substituent groups, and the aforementioned substituent groups are preferably selected from alkyl groups which have from 1 to 30 carbon atoms.

Preferably, the heterocyclic rings which may have substituent groups are selected from five-membered and six-membered heterocyclic rings.

H

It is even more preferred that the five-membered rings are selected from the group comprising the tetrazole, triazole, pyrazole, pyrazolidine, imidazole, oxazolidine, thiazolidine, pyrrolidine, pyrroline and pyrrole rings and that the six-membered heterocyclic rings are selected from the group comprising the piperazine, pyrazine, thiomorpholine, thiazine, morpholine, oxazine and piperidine rings.

Further it is preferred that both $A^1$ and $A^2$ are:

(1-pyrrolidinyl groups).

In a further aspect, the present invention provides the use of the organic molybdenum compounds as friction-modifiers.

In another aspect the present invention provides lubricating compositions which contain the organic molybdenum compounds.

The organic molybdenum compounds of this invention can be obtained, for example, by means of the methods outlined below.

When $A^1$ and $A^2$ are the same:

When $A^1$ and $A^2$ are different:

In a case where the aforementioned $A^1$ or $A^2$ is a five-member ring, then $A^1$ or $A^2$ can be represented by:

In this formula $Z^1$ to $Z^4$ are elements each selected individually from among the group comprising C, O, N and S, and in the case of C and N among these, adjacent C and N may form a double bond. $R^1$ to $R^4$ and $R^{1'}$ to $R^{4'}$ are groups each selected individually from the group comprising hydrogen and alkyl groups which have from 1 to 30 carbon atoms, but these groups are not present in those cases the bonding capacity is saturated by $Z^1$ to $Z^4$ forming a ring.

In a case where the aforementioned $A^1$ or $A^2$ is a six-membered ring, then $A^1$ or $A^2$ can be represented by:

In this formula $Z^5$ to $Z^9$ are elements each selected individually from among the group comprising C, O, N and S, and in the case of C and N among these, adjacent C and N may form a double bond. $R^5$ to $R^9$ and $R^{5'}$ to $R^{9'}$ are groups each selected individually from the group comprising hydrogen and alkyl groups which have from 1 to 30 carbon atoms, but these groups are not present in those cases the bonding capacity is saturated by $Z^5$ to $Z^9$ forming a ring.

The cases indicated below can be cited as actual examples of the aforementioned $A^1$ and $A^2$.

TABLE 1

In the case of a five-membered ring

|  | $Z^1$ | $Z^2$ | $Z^3$ | $Z^4$ |
|---|---|---|---|---|
| Tetrazole | C | N | N | N |
| Triazole | N | C | N | C |
| Pyrazole | N | C | C | C |
| Pyrazolidine | N | C | C | C |
| Imidazole | C | N | C | C |
| Oxazolidine | C | O | C | C |
| Thiazolidine | C | S | C | C |
| Pyrrolidine | C | C | C | C |
| Pyrroline | C | C | C | C |
| Pyrrole | C | C | C | C |

TABLE 2

In the case of a six-membered ring

|  | Z5 | Z6 | Z7 | Z8 | Z9 |
|---|---|---|---|---|---|
| Piperazine | C | C | N | C | C |
| Pyrazine | C | C | N | C | C |
| Thiomorpholine | C | C | S | C | C |
| Thiazine | C | C | S | C | C |
| Morpholine | C | C | O | C | C |
| Oxazine | C | C | O | C | C |
| Piperidine | C | C | C | C | C |

There may be substituent groups represented by $R^1$ to $R^9$ on the aforementioned five-membered rings such as a tetrazole ring or six-membered rings such as a morpholine ring. The alkyl groups which have from 1 to 30 carbon atoms may be linear chain or branched chain groups. These groups include, for example, methyl, ethyl, n-propyl, isopropyl, n-butyl, sec-butyl, t-butyl, n-heptyl, n-hexyl, n-octyl, 2-ethylhexyl, n-nonyl, n-decyl, n-undecyl, n-dodecyl, n-tridecyl, n-tetradecyl, n-hexadecyl, n-pentadecyl, n-octadecyl, n-nonadecyl and n-eicosyl.

The compounds of this invention can be broadly classified into the types I to V.

Type I
The case where $A^1$ is five-membered ring and $A^2$ is:

Moreover, $R^{10}$ and $R^{11}$ are groups each selected individually from among the group comprising hydrogen and the alkyl groups which have from 1 to 30 carbon atoms.

Type II
The case where $A^1$ is six-membered ring and $A^2$ is:

Type III
The case where $A^1$ and $A^2$ are both five-membered rings.

Type IV
The case where $A^1$ and $A^2$ are both six-membered rings.

Type V
The case where $A^1$ is a six-membered ring and $A^2$ is a five-membered ring.

In more practical terms, the group of compounds indicated below can be shown as compounds of Type I.

Below, $R^1$ to $R^4$ and $R^{1'}$ to $R^{4'}$ in these formulae are each individually a group selected from the group comprising hydrogen and alkyl groups, and the aforementioned alkyl groups are those which have from 1 to 30, preferably from 1 to 20 and most desirably from 1 to 10 carbon atoms, and hydrogen is the preferred one of these groups. Moreover, $R^{10}$ and $R^{11}$ are each individually groups which have been selected from the group comprising alkyl groups which have from 1 to 30, preferably from 1 to 20 and most desirably from 1 to 8 carbon atoms.

I-1

I-2

I-3

I-4

I-5

I-6

I-7

I-8

I-9

I-10

In more practical terms, the group of compounds indicated below can be shown as compounds of Type II.

II-1

II-2

II-3

II-4

II-5

II-6

II-7

Moreover, $R^5$ to $R^9$ and $R^{5'}$ to $R^{9'}$ in these formulae are each individually a group selected from the group comprising hydrogen and alkyl groups, and the aforementioned alkyl groups are those which have from 1 to 30, preferably from 1 to 20 and most desirably from 1 to 10 carbon atoms, and hydrogen is the preferred one of these groups. Moreover, $R^{10}$ and $R^{11}$ are each individually groups which have been selected from the group comprising alkyl groups which have from 1 to 30, preferably from 1 to 20 and most desirably from 1 to 8 carbon atoms.

The compounds where $A^1$ and $A^2$ have the structures indicated below can be cited as compounds of Type III.

III-1

III-2

III-3

III-4

III-5

III-6

III-7

III-8

III-9

III-10

III-11

III-29

III-30

III-31

III-32

III-33

III-34

III-35

III-36

III-37

III-38

III-39

III-40

III-41

III-42

III-43

III-44

III-45

III-46

III-47

III-48

III-49

III-50

III-51

III-52

III-53

III-54

III-55

Moreover, $R^1$ to $R^4$, $R^{1'}$ to $R^{4'}$, $R^{12}$ to $R^{15}$ and $R^{12'}$ to $R^{15'}$ in these formulae are each individually a group selected from the group comprising hydrogen and alkyl groups, and the aforementioned alkyl groups are those which have from 1 to 30, preferably from 1 to 20 and most desirably from 1 to 10 carbon atoms. Furthermore, hydrogen is the preferred one of these groups.

The compounds where $A^1$ and $A^2$ have the structures indicated below can be cited as compounds of Type IV.

IV-1

IV-2

IV-3

Moreover, $R^5$ to $R^9$, $R^{5'}$ to $R^{9'}$, $R^{16}$ to $R^{20}$ and $R^{16'}$ to $R^{20'}$ in these formulae are each individually a group selected from the group comprising hydrogen and alkyl groups, and the aforementioned alkyl groups are those which have from 1 to 30, preferably from 1 to 20 and most desirably from 1 to 10 carbon atoms. Furthermore, hydrogen is the preferred one of these groups.

The compounds where $A^1$ and $A^2$ have the structures indicated below can be cited as compounds of Type V.

-continued

V-6

V-7

V-8

V-9

V-10

V-11

V-12

V-13

-continued

V-14

V-15

V-16

V-17

V-18

V-19

V-20

V-21

-continued

V-22

V-23

V-24

V-25

V-26

V-27

V-28

V-29

-continued

V-30

V-31

V-32

V-33

V-34

V-35

V-36

V-37

-continued

V-38

V-39

V-40

V-41

V-42

V-43

V-44

V-45

-continued

V-46

V-47

V-48

V-49

V-50

V-51

V-52

V-53

V-70

$A^1$ is (shown structure), $A^2$ is (shown structure)

Moreover, $R^5$ to $R^9$, $R^{5'}$ to $R^{9'}$, $R^{12}$ to $R^{15}$ and $R^{12'}$ to $R^{15'}$ in these formulae are each individually a group selected from the group comprising hydrogen and alkyl groups, and the aforementioned alkyl groups are those which have from 1 to 30, preferably from 1 to 20 and most desirably from 1 to 10 carbon atoms. Furthermore, hydrogen is the preferred one of these groups.

Actual Compounds of Type I are:

Tetrazoyldithiocarbamate/dithioalkylcarbamate dioxymolybdenum complex, triazoylthiocarbamate/dithioalkylcarbamate dioxymolybdenum complex, pyrazoyldithio-carbamate/dithioalkylcarbamate dioxymolybdenum complex, pyrazolidyldithiocarbamate/dithioalkylcarbamate dioxymolybdenum complex, imidazoyldithiocarbamate/dithioalkylcarbamate dioxymolybdenum complex, oxazolyldithiocarbamate/dithioalkylcarbamate dioxymolybdenum complex, thiazolidyldithiocarbamate/dithioalkylcarbamate dioxymolybdenum complex, pyrrolidinyl-dithiocarbamate/dithioalkylcarbamate dioxymolybdenum complex, pyrrolinyldithiocarbamate/dithioalkylcarbamate dioxymolybdenum complex and pyrrolyldithiocarbamate/dithioalkylcarbamate dioxymolybdenum complex.

In the names of the illustrative compounds of Type I the alkyl groups are from C1 to C30 alkyl groups, and these include, for example, the methyl group and the ethyl group and the alkyl groups which have from 3 to 30 carbon atoms, including propyl, butyl, pentyl, hexyl, heptyl, octyl, nonyl, decyl, undecyl, dodecyl, tridecyl, tetradecyl, pentadecyl, hexadecyl, hepadecyl, octadecyl, nonadecyl, eicosyl, heneicosyl, docosyl, tricosyl, tetracosyl, pentacosyl, hexacosyl, heptacosyl, octacosyl, nonacosyl and triacontacyl groups which include normal and iso-forms.

Actual Compounds of Type II are:

Piperazyldithiocarbamate/dithioalkylcarbamate dioxymolybdenum complex, pyrazyldithiocarbamate/dithioalkylcarbamate dioxymolybdenum complex, thiomorpholyldithiocarbamate/dithioalkylcarbamate dioxymolybdenum complex, thiazyldithiocarbamate/dithioalkylcarbamate dioxymolybdenum complex, morpholyldithiocarbamate/dithioalkylcarbamate dioxymolybdenum complex, oxazyldithiocarbamate/dithioalkylcarbamate dioxymolybdenum complex and piperidyldithiocarbamate/dithioalkylcarbamate dioxymolybdenum complex.

In the names of the illustrative compounds of Type II the alkyl groups are from C1 to C30 alkyl groups, and these include, for example, the methyl group and the ethyl group and the alkyl groups which have from 3 to 30 carbon atoms, including propyl, butyl, pentyl, hexyl, heptyl, octyl, nonyl, decyl, undecyl, dodecyl, tridecyl, tetradecyl, pentadecyl, hexadecyl, hepadecyl, octadecyl, nonadecyl, eicosyl, heneicosyl, docosyl, tricosyl, tetracosyl, pentacosyl, hexacosyl, heptacosyl, octacosyl, nonacosyl and triacontacyl groups which include normal and iso-forms.

Actual Compounds of type III are:

Tetrazoyldithiocarbamate/tetrazolyldithiocarbamate di-oxymolybdenum, tetrazoylditiocarbamate/triazoyldithiocarbamate dioxymolybdenum complex, tetrazoyldithiocarbamate/pyrazoyldithiocarbamate dioxymolybdenum complex, tetrazoyldithiocarbamate/pyrazolidyldithiocarbamate dioxymolybdenum complex, tetrazoyldithiocarbamate/imidazoyldithiocarbamate dioxymolybdenum complex, tetrazoyldithiocarbamate/oxazolyldithiocarbamate dioxymolybdenum complex, tetrazoyldithiocarbamate/thiazolidyldithiocarbamate dioxymolybdenum complex, tetrazoyldithiocarbamate/pyrrolidinyldithiocarbamate dioxymolybdenum complex, tetrazoyldithiocarbamate/pyrrolinyldithiocarbamate dioxymolybdenum complex, tetrazoyldithiocarbamate/pyrrolyldithiocarbamate dioxymolybdenum complex, triazoyldithiocarbamate/triazoyldithiocarbamate dioxymolybdenum complex, triazolyldithiocarbamate/pyrazoyldithiocarbamate dioxymolybdenum complex, triazoyldithiocarbamate/pyrazolidyldithiocarbamate dioxymolybdenum complex, trizoyldithiocarbamate/imidazoyldithiocarbamate dioxymolybdenum complex, triazoyldithiocarbamate/oxazolyldithiocarbamate dioxymolybdenum complex, triazoyldithiocarbamate/thiazolidyldithiocarbamate dioxymolybdenum complex, triazoyldithiocarbamate/pyrrolidinyldithiocarbamate dioxymolybdenum complex, triazoyldithiocarbamate/pyrrolinyldithiocarbamate dioxymolybdenum complex, triazoyldithiocarbamate/pyrrolyldithiocarbamate dioxymolybdenum complex, pyrazoyldithiocarbamate/pyrazoyldithiocarbamate dioxymolybdenum complex, pyrazoyldithiocarbamate/pyrazolidyldithiocarbamate dioxymolybdenum complex, pyrazoyldithiocarbamate/imidazoyldithiocarbamate dioxymolybdenum complex, pyrazoyldithiocarbamate/oxazolyldithiocarbamate dioxymolybdenum complex, pyrazoyldithiocarbamate/thiazolidyldithiocarbamate dioxymolybdenum complex, pyrazoyldithiocarbamate/pyrrolidinyldithiocarbamate dioxymolybdenum complex, pyrazoyldithiocarbamate/pyrrolinyldithiocarbamate dioxymolybdenum complex, pyrazoyldithiocarbamate/pyrrolyldithiocarbamate dioxymolybdenum complex, pyrazolidyldithiocarbamate/pyrazolidyldithiocarbamate dioxymolybdenum complex, pyrazolidyldithiocarbamate/imidazoyldithiocarbamate dioxymolybdenum complex, pyrazolidyldithiocarbamate/oxazolyldithiocarbamate dioxymolybdenum complex, pyrazolidyldithiocarbamate/thiazoyldithiocarbamate dioxymolybdenum complex, pyrazolidyldithiocarbamate/pyrrolidinyldithiocarbamate dioxymolybdenum complex, pyrazolidyldithiocarbamate/pyrrolinyldithiocarbamate dioxymolybdenum complex, pyrazolidyldithiocarbamate/pyrrolyldithiocarbamate dioxymolybdenum complex, imidazoyldithiocarbamate/imidazoyldithiocarbamate dioxymolybdenum complex, imidazoyldithiocarbamate/oxazolyldithiocarbamate dioxymolybdenum complex, imidazoyldithiocarbamate/thiazolidyldithiocarbamate dioxymolybdenum complex, imidazoyldithiocarbamate/pyrrolidinyldithiocarbamate dioxymolybdenum complex, imidazoyldithiocarbamate/pyrrolinyldithiocarbamate dioxymolybdenum complex, imidazoyldithiocarbamate/pyrrolyldithiocarbamate dioxymolybdenum complex, oxazolyldithiocarbamate/oxazolyldithiocarbamate dioxymolybdenum complex, oxazolyldithiocarbamate/thiazolidyldithiocarbamate dioxymolybdenum complex, oxazolyldithiocarbamate/pyrrolidinyldithiocarbamate dioxymolybdenum complex, oxazolyldithiocarbamate/pyrrolinyldithiocarbamate dioxymolybdenum complex, oxazolyldithiocarbamate/pyrrolyldithiocarbamate dioxymolybdenum complex, thiazolidyldithiocarbamate/thiazolidyldithiocarbamate dioxymolybdenum complex, thiazoylidyldithiocarbamate/ pyrrolidinyldithiocarbamate dioxymolybdenum complex, thiazoylidyldithiocarbamate/pyrrolinyldithiocarbamate dioxymolybdenum complex, thiazolidyldithiocarbamate/pyrrolyldithiocarbamate dioxymolybdenum complex, pyrrolidinyldithiocarbamate/pyrrolidinyldithiocarbamate dioxymolybdenum complex, pyrrolidinyldithiocarbamate/pyrrolinyldithiocarbamate dioxymolybdenum complex, pyrrolidinyldithiocarbamate/pyrrolinyldithiocarbamate dioxymolybdenum complex, pyrrolinyldithiocarbamate/pyrrolinyldithiocarbamate dioxymolybdenum complex, pyrrolinyldithiocarbamate/pyrrolinyldithiocarbamate dioxomolybdenum complex, pyrrolyldithiocarbamate/pyrrolyldithiocarbamate dioxymolybdenum complex and pyrrolyldithiocarbamate/pyrrolyldithiocarbamate dioxy-molybdenum complex.

Typical Compounds of Type IV are:

Piperazyldithiocarbamate/piperazyldithiocarbamate dioxymolybdenum complex, piperazyldithiocarbamate/pyrazyldithiocarbamate dioxymolybdenum complex, piperazyldithiocarbamate/thiomorpholyldithiocarbamate dioxymolybdenum complex, piperazyldithiocarbamate/thiazyldithiocarbamate dioxymolybdenum complex, piperazyldithiocarbamate/morpholyldithiocarbamate dioxymolybdenum complex, piperazyldithiocarbamate/oxazyldithiocarbamate dioxymolybdenum complex, piperazyldithiocarbamate/piperidyldithiocarbamate dioxymolybdenum complex, pyrazyldithiocarbamate/pyrazyldithiocarbamate dioxymolybdenum complex, pyazyldithiocarbamate/thiomorpholyldithiocarbamate, dioxymolybdenum complex, pyrazyldithiocarbamate/thiazyldithiocarbamate dioxymolybdenum complex, pyrazyldithiocarbamate/morpholyldithiocarbamate dioxymolybdenum complex, pyrazyldithiocarbamate/oxazyldithiocarbamate dioxymolybdenum complex, pyrazyldithiocarbamate/piperidyldithiocarbamate dioxymolybdenum complex, thiomorpholyldithiocarbamate/thiomorpholyldithiocarbamate dioxymolybdenum complex, thiomorpholyldithiocarbamate/thiazyldithiocarbamate dioxymolybdenum complex, thiomorpholyldithiocarbamate/morpholyldithiocarbamate dioxymolybdenum complex, thiomorpholyldithiocarbamate/oxazyldithiocarbamate dioxymolybdenum complex, thiomorpholyldithiocarbamate/piperidyldithiocarbamate dioxymolybdenum complex, thiazyldithiocarbamate/thiazyldithiocarbamate dioxymolybdenum complex, thiazyldithiocarbamate/morpholyldithiocarbamate dioxymolybdenum complex, thiazyldithiocarbamate/oxazyldithiocarbamate dioxymolybdenum complex, thiazyldithiocarbamate/piperidyldithiocarbamate dioxymolybdenum complex, morpholyldithiocarbamate/morpholyldithiocarbamate dioxymolybdenum complex, morpholyldithiocarbamate/oxalyldithiocarbamate dioxymolybdenum complex, morpholyl-dithiocarbamate/piperidyldithiocarbamate dioxymolybdenum complex, oxazyldithiocarbamate/oxazyldithiocarbamate dioxymolybdenum complex, oxazyldithio-carbamate/piperidyldithiocarbamate dioxymolybdenum complex and piperidyldithiocarbamate/piperidyldithiocarbamate dioxymolybdenum complex.

Typical Compounds of Type V are:

Piperazyldithiocarbamate/tetrazoyldithiocarbamate dioxymolybdenum complex, piperazyldithiocarbamate/triazoyldithiocarbamate dioxymolybdenum complex, piperazyldithiocarbamate/pyrazoyldithiocarbamate dioxymolybdenum complex, piperazyldithiocarbamate/pyrazolidyldithiocarbamate dioxymolybdenum complex, piperazyldithiocarbamate/imidazoyldithiocarbamate dioxymolybdenum complex, piperazyldithiocarbamate/oxazolyldithiocarbamate dioxymolybdenum complex, piperazyldithiocarbamate/thiazolidyldithiocarbamate dioxymolybdenum complex, piperazyldithiocarbamate/pyrolidinyldithiocarbamate dioxymolybdenum complex, piperazyldithiocarbamate/pyrrolinyldithiocarbamate dioxymolybdenum complex, piperazyldithiocarbamate/pyrrolyldithiocarbamate dioxymolybdenum complex, pyrazyldithiocarbamate/tetrazoyldithiocarbamate dioxymolybdenum complex, pyrazyldithiocarbamate/triazoyldithiocarbamate dioxymolybdenum complex, pyrazyldithiocarbamate/pyrazoyldithiocarbamate dioxymolybdenum complex, pyrazyldithiocarbamate/pyrazolidyldithiocarbamate dioxymolybdenum complex, pyrazyldithiocarbamate/imidazoyldithiocarbamate dioxymolybdenum complex, pyrazyldithiocarbamate/oxazolyldithiocarbamate dioxymolybdenum complex, pyrazyldithiocarbamate/thiazolidyldithiocarbamate dioxymolybdenum complex, pyrazyldithiocarbamate/pyrrolidinyldithiocarbamate dioxymolybdenum complex, pyrazyldithiocarbamate/pyrrolinyldithiocarbamate dioxymolybdenum complex, pyrazyldithiocarbamate/pyrrolyldithiocarbamate dioxymolybdenum complex, thiomorpholyldithiocarbamate/tetrazoyldithiocarbamate dioxymolybdenum complex, thiomorpholyldithiocarbamate/triazoyldithiocarbamate dioxymolybdenum complex, thiomorpholyldithiocarbamate/pyrazoyldithiocarbamate dioxymolybdenum complex, thiomorpholyldithiocarbamate/pyrazolidyldithiocarbamate dioxymolybdenum complex, thiomorpholyldithiocarbamate/imidazoyldithiocarbamate dioxymolybdenum complex, thiomorpholyldithiocarbamate/oxazolyldithiocarbamate dioxymolybdenum complex, thiomorpholyldithiocarbamate/thiazolidyldithiocarbamate dioxymolybdenum complex, thiomorpholyldithiocarbamate/pyrrolidinyldithiocarbamate dioxymolybdenum complex, thiomorpholyldithiocarbamate/pyrrolinyldithiocarbamate dioxymolybdenum complex, thiomorpholyldithiocarbamate/pyrrolyldithiocarbamate dioxymolybdenum complex, thiazyldithiocarbamate/tetrazoyldithiocarbamate dioxymolybdenum complex, thiazyldithiocarbamate/triazoyldithiocarbamate dioxymolybdenum complex, thiazyldithio-carbamate/pyrazoyldithiocarbamate dioxymolybdenum complex, thiazyldithiocarbamate/-pyrazolidyldithiocarbamate dioxymolybdenum complex, thiazyldithio-carbamate/imidazoyldithiocarbamate dioxymolybdenum complex, thiazyldithio-carbamate/oxazolyldithiocarbamate dioxymolybdenum complex, thiazyldithio-carbamate/thiazolidyldithiocarbamate dioxymolybdenum complex, thiazyldithio-carbamate/pyrolidinyldithiocarbamate dioxymolybdenum complex, thiazyldithio-carbamate/pyrrolinyldithiocarbamate dioxymolybdenum complex, thiazyldithio-carbamate/pyrrolyldithiocarbamate dioxymolybdenum complex, morpholyldithio-carbamate/tetrazoyldithiocarbamate dioxymolybdenum complex, morpholyldithio-carbamate/triazoyldithiocarbamate dioxymolybdenum complex, morpholyldithio-carbamate/pyrazoyldithiocarbamate dioxymolybdenum complex, morpholyldithio-carbamate/pyrazolidyldithiocarbamate dioxymolybdenum complex, morpholyldithio-carbamate/imidazoyldithiocarbamate dioxymolybdenum complex, morpholyldithio-carbamate/oxazolyldithiocarbamate dioxymolybdenum complex, morpholyldithio-carbamate/thiazolidyldithiocarbamate dioxymolybdenum complex, morpholyldithio-carbamate/pyrrolidinyldithiocarbamate dioxymolybdenum complex, morpholyldithio-carbamate/pyrrolinyldithiocarbamate dioxymolybdenum complex, morpholyldithio-carbamate/pyrrolyldithiocarbamate dioxymolybdenum complex, oxazyldithio-carbamate/tetrazoyldithiocarbamate dioxymolybdenum complex, oxazyldithio-carbamate/triazoyldithio-carbamate dioxymolybdenum complex, oxazyldithiocarbamate/-pyrazoyldithiocarbamate dioxymolybdenum complex, oxazyldithio-carbamate/pyrazolidyldithiocarbamate dioxymolybdenum complex, oxazyldithio-carbamate/imidazoyldithiocarbamate dioxymolybdenum complex, oxazyldithio-carbamate/oxazolyldithiocarbamate dioxymolybdenum complex, oxazyldithio-carbamate/thiazolidyldithiocarbamate dioxymolybdenum complex, oxazyldithio-carbamate/pyrrolidinyldithiocarbamate dioxymolybdenum complex, oxazyldithio-carbamate/pyrrolinyldithiocarbamate dioxymolybdenum complex, oxazyldithio-carbamate/pyrrolyldithiocarbamate dioxymolybdenum complex, piperidyldithio-carbamate/tetrazoyldithiocarbamate dioxymolybdenum complex, piperidyldithio-carbamate/triazoyldithiocarbamate dioxymolybdenum complex, piperidyldithio-carbamate/pyrazoyldithiocarbamate dioxymolybdenum complex, piperidyldithio-carbamate/pyrazolidyldithiocarbamate dioxymolybdenum complex, piperidyldithio-carbamate/imidazoyldithiocarbamate dioxymolybdenum complex, piperidyldithio-carbamate/oxazolyldithiocarbamate dioxymolybdenum complex, piperidyldithio-carbamate/thiazolidyldithiocarbamate dioxymolybdenum complex, piperidyldithio-carbamate/pyrrolidinyldithiocarbamate dioxymolybdenum complex, piperidyldithio-carbamate/pyrrolinyldithiocarbamate dioxymolybdenum complex and piperidyldithio-carbamate/pyrrolyldithiocarbamate dioxymolybdenum complex.

Lubricating oils and greases, for example, can be cited as lubricating composition of this invention. The amount of the compound of this invention in a lubricating composition is the same as with the conventional friction-modifiers, for example, being compounded in a proportion with respect to the composition generally of some 0.1 to 10 wt %.

There are no particular limitations regarding the base oil or grease used in lubricating composition according to the present invention, and various conventional greases, mineral oils and synthetic oils may be conveniently used. For the purpose of this description, the term "base oil" is meant to also include a grease base stock.

The base oil used in the present invention may conveniently comprise mixtures of one or more mineral oils and/or one or more synthetic oils.

Mineral oils include liquid petroleum oils and solvent-treated or acid-treated mineral lubricating oil of the paraffinic, naphthenic, or mixed paraffinic/naphthenic type which may be further refined by hydrofinishing processes and/or dewaxing.

Suitable base oils for use in the lubricating oil composition of the present invention are Group I, Group II or Group III base oils, polyalphaolefins, Fischer-Tropsch derived base oils and mixtures thereof.

By "Group I" base oil, "Group II" base oil and "Group III" base oil in the present invention are meant lubricating oil base oils according to the definitions of American Petroleum Institute (API) categories I, II and III. Such API categories are defined in API Publication 1509, 15th Edition, Appendix E, April 2002.

Suitable Fischer-Tropsch derived base oils that may be conveniently used as the base oil in the lubricating oil composition of the present invention are those as for example disclosed in EP 0 776 959, EP 0 668 342, WO 97/21788, WO 00/15736, WO 00/14188, WO 00/14187, WO 00/14183, WO 00/14179, WO 00/08115, WO 99/41332, EP 1 029 029, WO 01/18156 and WO 01/57166.

Synthetic oils include hydrocarbon oils such as olefin oligomers (PAOs), dibasic acid esters, polyol esters, and dewaxed waxy raffinate. Synthetic hydrocarbon base oils sold by the Shell Group under the designation "XHVI" (trade mark) may be conveniently used.

EFFECTS OF THE INVENTION

(1) Novel phosphorus-free Mo-based friction-modifiers have been obtained.
(2) When compared with the existing Mo-based friction-reducing agents with the same Mo content in the oil, the compounds of this invention exhibit a lower coefficient of friction, and they can be used as additives for various types of energy-saving lubricating oil. See FIG. 1 hereafter.
(3) The compounds of this invention are especially suitable for use as friction-modifiers for fuel-saving engine oils as they are phosphorus-free.

ILLUSTRATIVE EXAMPLES

The present invention is described below by means of Examples and Comparative Examples but the invention is not limited in any way by these examples.

Example 1

The synthesis of the compound indicated below, a compound where both $A^1$ and $R^2$ are:

The method of production outlined below is an example and production is not limited to just this method.

Sodium molybdate (7.3 g, 0.03 mol) and ammonium pyrrolidinedithiocarbamate (9.9 g, 0.06 mol) were added to a 500 ml pear-shaped flask and dissolved in 100 ml of water. Then 300 ml of 0.12 mol dilute hydrochloric acid was added dropwise from a dropping funnel over a period of about 2 hours. The precipitated material obtained was recovered by suction filtration and washed thoroughly with water, ether, methanol, acetone and the water was removed. Moreover, the material was left to stand in a desiccator under vacuum for 2 days to eliminate the water fraction. Recrystallization was carried out using dichloromethane/methanol.

The target compound was a yellow coloured powder and the yield was 72%.

The compound which had been produced was analyzed using NMR and Mass spectrometry and verification that the target compound had been produced was carried out.

$^1$H NMR (CDCl$_2$) δ=2.08-2.11 (m, 2H×4), 3.75-3.78 (m, 2H×4)

Mass (EI$^+$, 70 eV) m/z (rel. intensity)=406 (M$^+$-0, 9) 422 (M$^+$, 3), 114 (100, C$_4$H$_8$NCS)

Example 2 and Comparative Example 1

The compound obtained in Example 1 was used in Example 2 and the compound with the chemical formula indicated below (trade name Naugalube Moly FM2543, produced by the Crompton Co.) was used in Comparative Example 1. The above compounds were added to provide a molybdenum content in each case of 500 ppm in API Group III mineral oil (viscosity at 100° C. 4.23 mm²/s) to which 5% of a dispersing agent (alkenyl succinic acid polyalkylene polyimide, trade name Infineum C9266) had been added.

Figure 1:
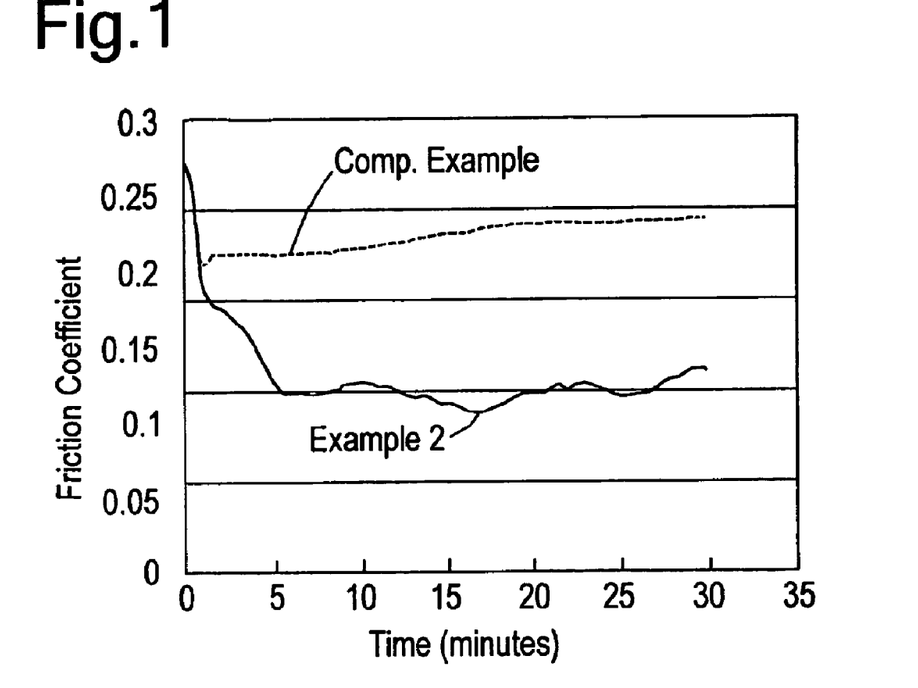
FIG. 1 is a graph which shows how the friction coefficient behaved with the passage of time with the sample oils of Example 2 and Comparative Example 1.
Figure 2:
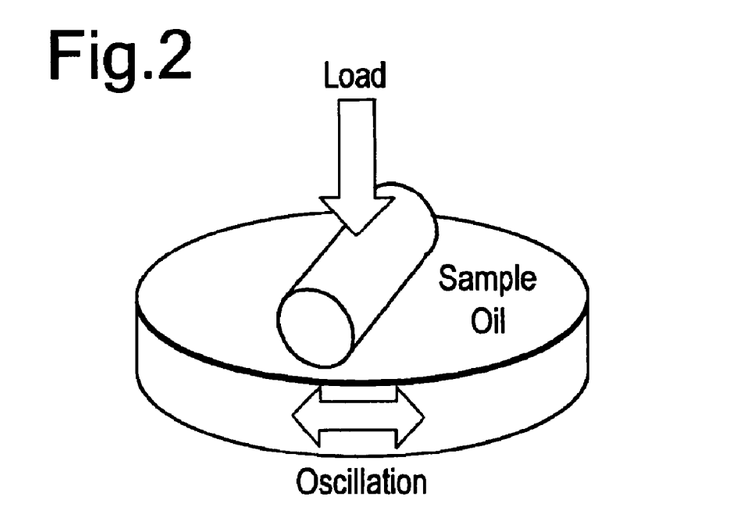
FIG. 2 is an outline drawing of the reciprocating movement tester of the cylinder-on-disc type which was used to measure the friction coefficients. In a first aspect, the present invention provides molybdenum compounds having the general formula (1) which is indicated below.

These sample oils were subjected to 30 minute friction coefficient measurement and evaluation under the conditions shown in Table 3 below using an SRV tester (a reciprocating movement tester of the cylinder-on-disc type shown in FIG. 2) and the results are shown in FIG. 1. The test piece was 52100 steel.

TABLE 3

| Condition | Parameter |
| --- | --- |
| Load | 400 N |
| Frequency | 50 Hz |
| Amplitude | 1.5 mm |
| Temperature | 100° C. |
| Sample Size | 0.1 mm³ |

TABLE 4

|  | Comparative Example 1 Naugalube Moly FM2543 | Example 2 Compound Obtained in Example 1 |
| --- | --- | --- |
| Mo Content in the Oil ppm | 500 | 500 |
| Alkenylsuccinic acid polyalkylene polyimide (%) | 5 | 5 |

What is claimed is:

1. An organic molybdenum compound having the general formula (1) below

General Formula (1)

(1)

wherein A¹ and A² are five-membered heterocyclic rings which may have substituent groups.

2. An organic molybdenum compound according to claim 1 wherein the aforementioned substituent groups are selected from alkyl groups having from 1 to 30 carbon atoms.

3. An organic molybdenum compound according to claim 1 wherein the five-membered rings are selected from the group comprising tetrazole, triazole, pyrazole, pyrazolidine, imidazole, oxazolidine, thiazolidine, pyrrolidine, pyrroline and pyrrole rings.

4. An organic molybdenum compound according to claim 1 in which both A¹ and A² are:

(1-pyrrolidinyl groups).

5. A lubricating composition comprising a base oil and the organic molybdenum compound according to claim 1.

6. Method of improving the friction characteristics of a lubricating composition by using the organic molybdenum compound according to claim 1.

* * * * *